United States Patent

Bather et al.

[11] Patent Number: 5,849,591
[45] Date of Patent: Dec. 15, 1998

[54] METHOD OF DETERMINING THE COMPONENT OF A GAS IN A GAS SAMPLE

[75] Inventors: Wolfgang Bather; Ingo Kaneblei, both of Lübeck; Matthias Martens, Gross Schenkenberg; Andreas Mohrmann, Krummesse; Ingo Pooch, Ratekau, all of Germany

[73] Assignee: Drägerwerk Aktiengesellschaft, Lübeck, United Kingdom

[21] Appl. No.: 854,987

[22] Filed: May 13, 1997

[30] Foreign Application Priority Data

May 14, 1996 [DE] Germany ............... 196 19 391.5

[51] Int. Cl.⁶ ............... G01N 33/00; G01N 21/00
[52] U.S. Cl. ............... 436/34; 422/59; 422/60; 422/86; 422/87; 422/88; 436/44; 436/121; 436/134; 436/164
[58] Field of Search ............... 422/59–60, 86–88; 436/34, 43, 44, 52, 121, 134, 164, 183

[56] References Cited

U.S. PATENT DOCUMENTS

| | | | |
|---|---|---|---|
| 3,870,469 | 3/1975 | Walker | 422/86 X |
| 4,059,405 | 11/1977 | Sodickson et al. | 436/44 |
| 4,123,227 | 10/1978 | Heim et al. | 436/134 |
| 4,127,780 | 11/1978 | Kimbell | 250/559.01 |
| 4,245,997 | 1/1981 | Wiesner | 422/86 X |
| 4,617,277 | 10/1986 | Bohl | 436/34 |
| 4,806,491 | 2/1989 | Heim | 422/87 X |
| 5,057,280 | 10/1991 | Stock et al. | 422/87 X |
| 5,397,538 | 3/1995 | Stark et al. | 436/44 X |

FOREIGN PATENT DOCUMENTS 0187898  7/1986  European Pat. Off.
2628790  11/1977  Germany.

OTHER PUBLICATIONS

K. Leichnitz Chem,–Ztg., Chem. Appar, 1967, 91, 141–148.
R. G. Smith et al. Health Lab. Sci. 1975 12, 171–172.
C.L. Kimbell et al. ASTM Spec. Tech. Publ. 1983, pp. 823, 41–49.
S. A. Momin et al. Anal. Proc. 1989, 26, 372–373.
"A Clinical Method for the Determination of Carbon Monoxide in Air "by T. Anderson et al, Science Tools, The LKB Instrument Journal, vol. 3, No. 1, Apr. 1958, p. 9–11.

*Primary Examiner*—Arlen Soderquist
*Attorney, Agent, or Firm*—Walter Ottesen

[57] ABSTRACT

The invention is directed to a method for determining the portion of a gaseous or vaporous component in a gas mixture utilizing a detecting substance which can enter into a chemical reaction with the component to produce a coloration of the detecting substance and utilizing a device for evaluating the coloration. The method includes the steps of: passing the gas mixture at a constant volume flow through a channel containing the detecting substance; detecting a reflectance signal I(t) within a defined spatially fixed length segment of the channel; determining a slope $\Delta I/\Delta t$ at the start of the chemical reaction during a time interval $\Delta t$ in which the detecting substance is present in excess; determining a saturation reflectance signal $I^{100}$ toward the end of the chemical reaction which corresponds to an almost complete chemical conversion of the detecting substance within the length segment; and, determining a normalized slope in correspondence to the formal relationship: $\Delta I/(I^{100}$

*$\Delta t$), which is proportional to the portion of the gaseous or vaporous component.

8 Claims, 4 Drawing Sheets

| c(ppm) | $\Delta t_m$ (sec) | s(%) | $1/\Delta t_m$ (1/sec) |
|---|---|---|---|
| 2 | 32,58 | 7,3 | 0,031 |
| 10 | 7,92 | 3,9 | 0,126 |
| 30 | 3,06 | 4,9 | 0,327 |
| 50 | 1,93 | 5,9 | 0,518 |

FIG. 3

METHOD OF DETERMINING THE COMPONENT OF A GAS IN A GAS SAMPLE

BACKGROUND OF THE INVENTION

So-called test tubes, which are filled with a powdery or granular chemical reagent, function, in general, to determine gaseous constituents in gas mixtures which are either drawn by suction through the tube or are pressed therethrough. In this operation, the tube changes color and the coloration advances in the direction of gas flow. The length of the colored zone is proportional to the quantity of the gas constituent to which the reagent specifically responds. When the quantity of the carrier gas pressed through or drawn by suction through the tube is known, then the concentration of the analyte in the carrier gas can be determined from the length of the colored zone. However, it is a disadvantage of the method that the evaluation of the zone is subjective as this can lead to errors which are too great when the color contrasts are blurred.

A further method, especially for measuring the CO concentration in air, utilizes the coloration of a reaction gel when CO is present in the air conducted through the test tube. The test tube is mounted in the beam path of a photometer. The time is measured which is needed for obtaining a specific attenuation of the radiation when passing through the layer of the reaction gel which takes on a coloring. This time, which is measured, is proportional to the CO concentration for a constant flow. A disadvantage of this method is the required high accuracy of positioning of the test tube in the photometer to fix the element of volume in which the chemical reaction takes place and the long measuring time needed because of the relatively high reagent volume element. Blurred color zones lead to reflections which change only very slowly and precise measurements are therefore not possible in such systems. The known method is disclosed in the article of T. Anderson et al entitled "A Clinical Method for the Determination of Carbon Monoxide in Air" published in The LKB Instrument Journal, Vol. 3, No. 1, April 1958, pages 9 to 11.

A method is described in German Patent 2,628,790 wherein a number of light barriers for scanning the tube are mounted along the tube at uniform spacings. The air sample is conducted through the tube at a constant flow and an analyte, which is present, can then react with the reagent while producing a change in color. With the aid of the light barriers, the speed of migration of the color front can be determined. This is a measure for the concentration of the analyte. However, it is a disadvantage of this method that sharp color zones must be formed for precise measurements. Furthermore, a precise positioning is required because the speed of migration is not only dependent upon the concentration of analyte present but also is dependent upon the location of the test tube because, for example, at the end of the test tube, the influence of the previous layer, which had already reacted chemically, is much greater than at the front end of the reagent layer.

In European patent publication 0,187,898, and in comparison to German Patent 2,628,790, a high resolution capacity is achieved by utilizing a light-sensitive diode array. Although the resolution capacity is improved, a blurred color front occurs essentially because of the chemical and physical characteristics of the analyte and of the reagent material. The disadvantage is that here too, only reagent systems having a sharp color front can be used.

SUMMARY OF THE INVENTION

It is an object of the invention to quickly and sensitively determine analyte concentrations.

The method of the invention is for determining the portion of a gaseous or vaporous component in a gas mixture utilizing a detecting substance which can enter into a chemical reaction with the component to produce a coloration of the detecting substance and utilizing a device for evaluating the coloration. The method includes the steps of: passing the gas mixture at a constant volume flow through a channel containing the detecting substance; detecting a reflectance signal I(t) within a defined spatially fixed length segment of the channel; determining a slope $\Delta I/\Delta t$ at the start of the chemical reaction during a time interval $\Delta t$ in which the detecting substance is present in excess; determining a saturation reflectance signal $I^{100\%}$ toward the end of the chemical reaction which corresponds to an almost complete chemical conversion of the detecting substance within the length segment; and, determining a normalized slope in correspondence to the formal relationship: $\Delta I/(I^{100\%}*\Delta t)$, which is proportional to the portion of the gaseous or vaporous component.

The advantage of the method of the invention is, most importantly, the following: the short measuring time, the usability of chemical reactions which have an unsharp color front, the objective evaluation of the chemical reaction and the in-situ standardization.

The method of the invention distinguishes from the known method disclosed in German Patent 2,628,790 in that: a spatial resolution is not required to detect a color front, that the measurement is carried out at a defined volume element filled with the detecting reagent; and, that the corresponding reflectance signal is utilized only in the linearly decreasing portion for measuring the concentration. The total chemical conversion within the volume element functions to normalize the reflectance signal. The glass capillary within a window is viewed as a volume element. The window exposes a defined length of the glass capillary. The window can be a cutout in a covering surrounding the glass capillary or it can be defined by a focusing optic.

BRIEF DESCRIPTION OF THE DRAWINGS

The invention will now be described with reference to the drawings wherein:

FIG. 3 is a table showing the results for hydrogen sulfide in air;

DESCRIPTION OF THE PREFERRED EMBODIMENTS OF THE INVENTION

Figure 1:
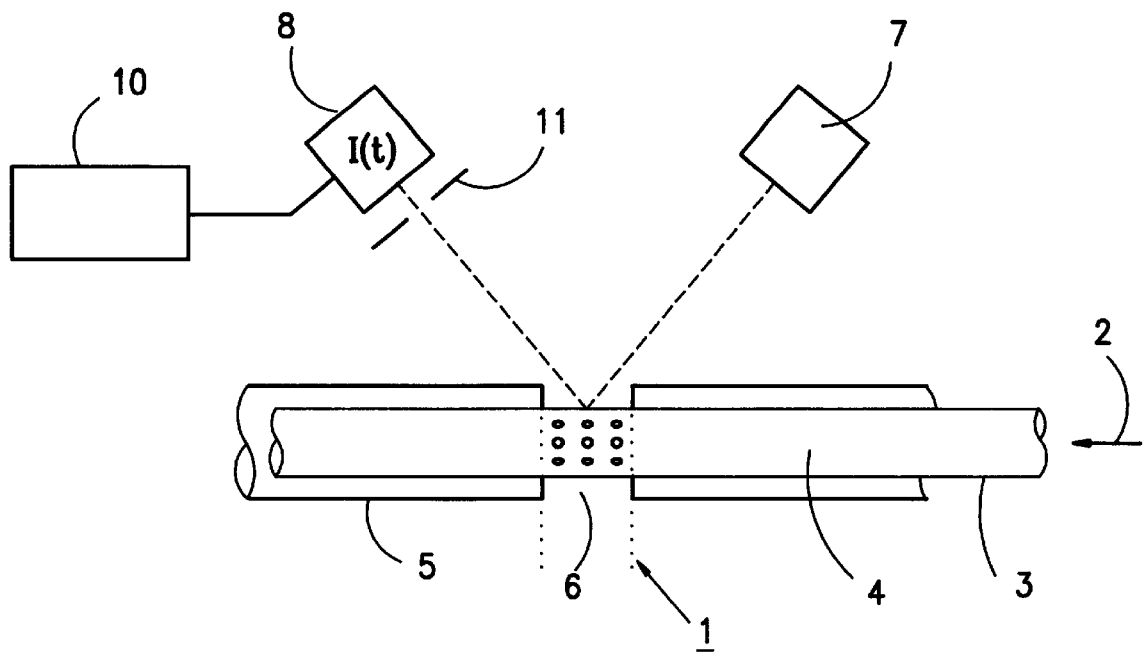
FIG. 1 is a schematic of a measuring apparatus having a glass capillary filled with a detecting reagent.

FIG. 1 shows a measuring apparatus 1 for determining the portion of a component to be detected in a gas sample. The gas sample is drawn through a glass capillary 3 in the direction of arrow 2. The glass capillary 3 has a defined and constant diameter and is filled with a fine-granular detecting substance 4. The glass capillary 3 is surrounded by a covering 5 having a window 6. The window 6 exposes a defined length of the glass capillary 3 for the evaluation of the coloration of the detecting substance 4. A defined volume element results from the length of the window 6 and the inner diameter of the glass capillary 3. The coloration is determined in the defined volume element. The detecting substance is schematically represented by small circles in the region of the window 6.

The coloration of the detecting substance is measured by means of a radiation transmitter 7 and a radiation receiver 8 in reflectance measurement. The radiation receiver 8 supplies a time-dependent reflectance signal I(t) to an evaluation unit 10. The evaluation unit can, for example, contain a microprocessor programmed to perform calculations of the method steps.

According to another feature of this invention, optic means for focusing the reflected radiation can be provided, for example, in the form of a slit diaphragm 11 mounted in front of the radiation receiver 8.

The number of detecting molecules which are available for the chemical reaction of the component to be detected is known because of the following: the constant diameter of the glass capillary 3, the homogeneous filling with the detecting substance 4 and the window 6 having a defined length. Product molecules arise in the chemical reaction of the detecting molecules with the component to be detected or with the analyte. The number of the product molecules is measured as a reflectance signal I(t).

With respect to the analyte molecules, which penetrate into the detecting substance 4 in the region of the window 6, the following processes can occur:

(a) they can react chemically;
(b) they can be adsorbed on the surface of the detecting substance;
(c) they can be absorbed by liquid phases which are possibly present; and,
(d) they can depart unchanged from the detecting substance in the region of the window 6.

Product molecules can only be detected on the basis of chemical reaction via the radiation receiver 8. For this reason, it has to be the object to select conditions in which the chemical reaction is determinative. This is the case as long as the detecting molecules are present in a great surplus to the analyte molecules, that is, at the start of the measuring process. Under these conditions, virtually all analyte molecules entering into the window 6 react chemically with the detecting molecules to form the product molecules observable with the radiation receiver 8. If a constant and an adequately small flow of the sample gas is provided at the same time, then an almost constant formation of the product molecules takes place and the trace of the curve of the reflectance signal forms an almost straight line.

Figure 2:
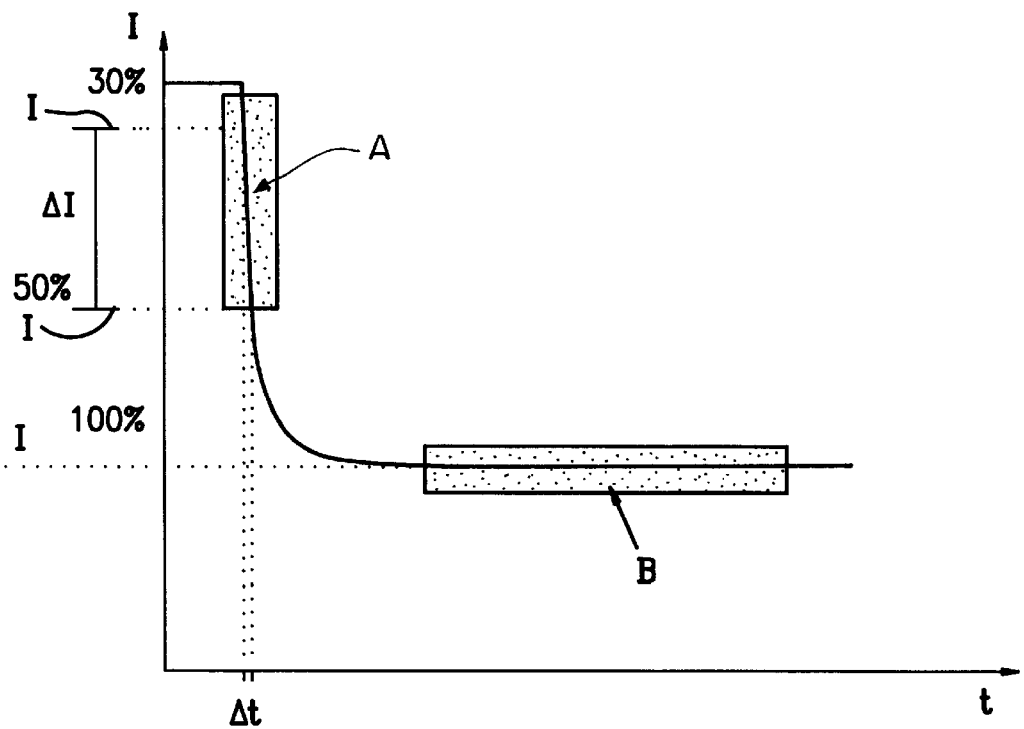
FIG. 2 is a graph of the reflectance signal I plotted as a function of time (t)

In FIG. 2, segment A of the reflectance signal I(t) corresponds to a straight line. Preferably, a slope $\Delta I/\Delta t$ is computed in this curve segment. In the further trace of the curve, the formation of the product molecules decreases until the reagent is finally consumed. An excess of analyte molecules compared to the detecting molecules is present in curve segment B. The chemical equilibrium is thereby shifted in the direction of the product molecules and the formed product molecules are almost equivalent to the pregiven and known detecting molecules. In this way, the reflectance signal obtained in curve segment B is equivalent to the number of the detecting molecules.

The quantity of the detecting substance 4 in the selected volume element is quantitatively known and the chemical conversion is equivalent and complete. For this reason, the corresponding reflectance signal $I^{100\%}$ can be used as a reference for a normalization. In this way, for example, intensity fluctuations of the reflectance light source are compensated. If the determined slope $\Delta I/\Delta t$ is normalized at $I^{100\%}$ and if this is plotted against the concentration (c), then a line, which is almost a straight line, is obtained under ideal conditions.

Usually, the reflectance signal I(t) between the values $I^{30\%}$ and $I^{50\%}$ is used for the determination of $\Delta I$.

In the table of FIG. 3, the results for the measurement of hydrogen sulphide in air are shown. In FIG. 3, (c) corresponds to the adjusted hydrogen sulphide concentration, $\Delta t_m$ corresponds to the mean value of times $\Delta t$ between the reflectance signal range of 30% to 50% of the 100% value of ten measurements (FIG. 2) and (s) corresponds to the standard deviation.

Figure 4:
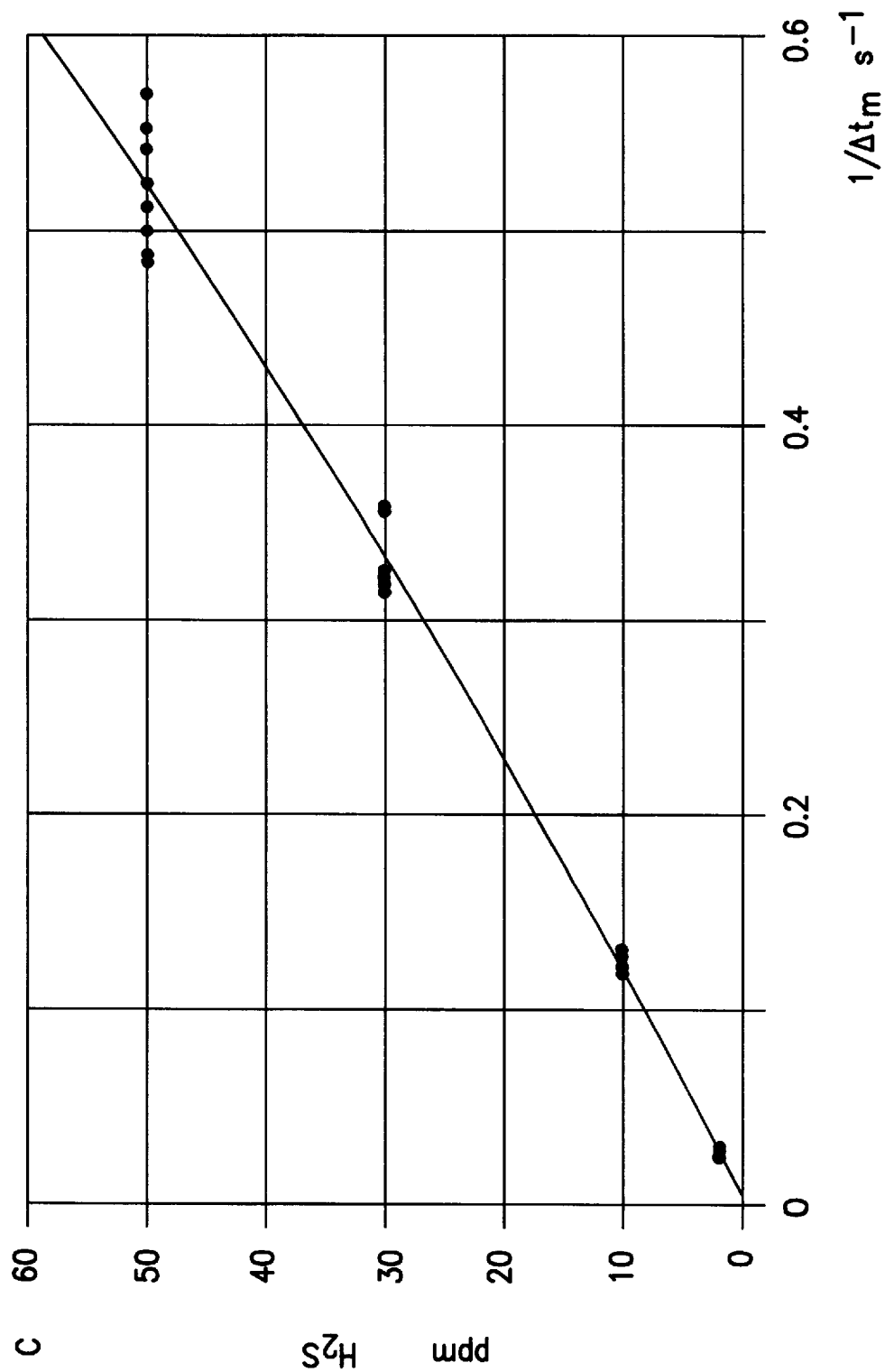
FIG. 4 is a graphic representation of the measuring results of FIG. 3.

In FIG. 4, the results for hydrogen sulphide in accordance with the table of FIG. 3 are shown. The concentration (c) is plotted against $1/\Delta t_m$. A slightly curved compensating line results which can be approximated by a polynome in an especially simple manner.

Deviations from a straight line are caused by an increasing influence of the adsorption effects of the analyte molecules on the detecting molecules.

Figure 5:
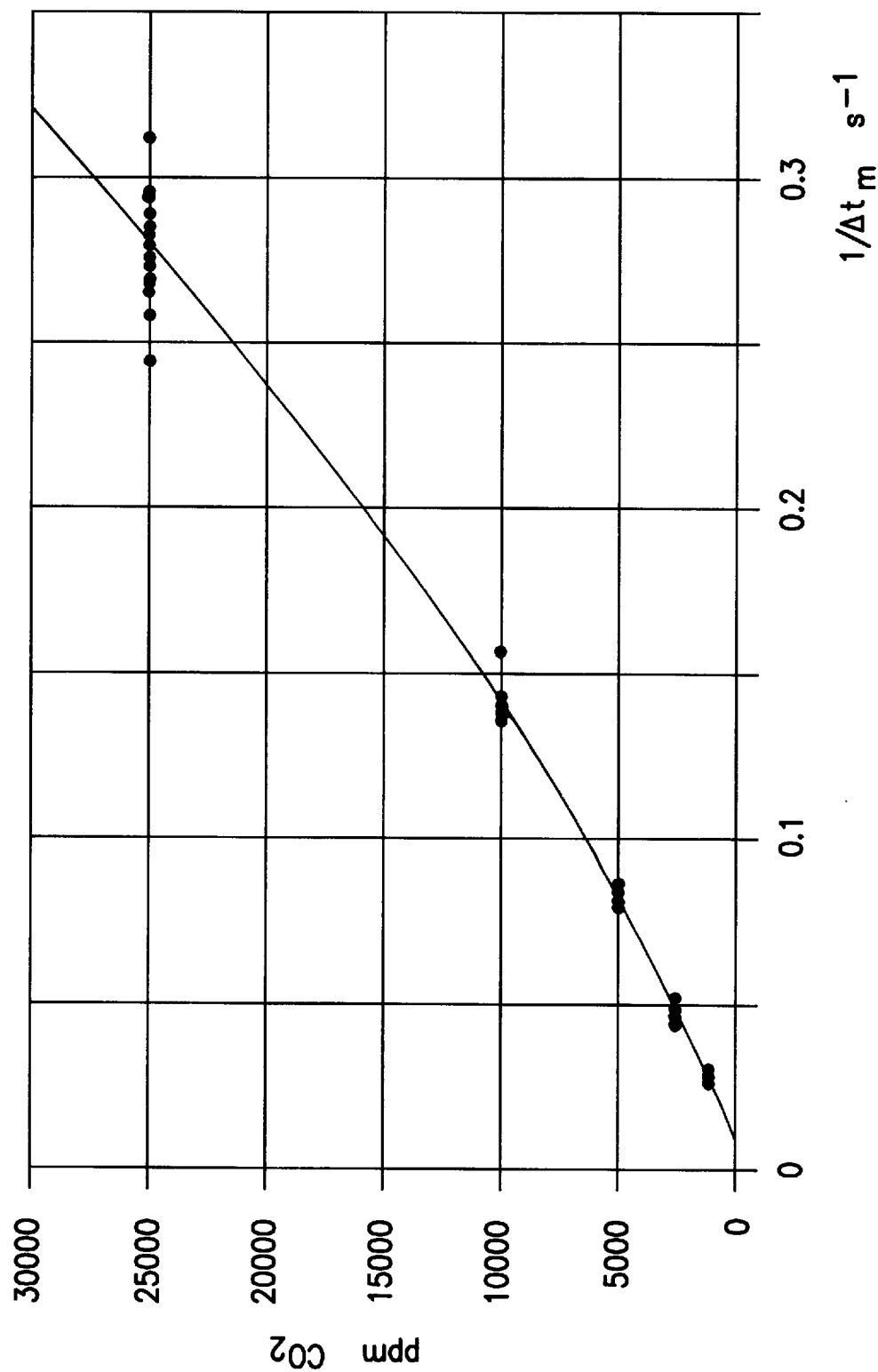
FIG. 5 is a graphic representation of the measuring results for carbon dioxide.

A calibration curve with such a curve form is shown in FIG. 5 for the detection of carbon dioxide in air.

The following operations are carried out in the evaluation unit (not shown):

(a) time dependent detection of the reflection signal I(t) which is directly proportional to the formation of the product molecules P;
(b) determination of the slope $\Delta I/\Delta t$ in a variable but defined window 6. This window 6 is determined by the presence of conditions in such a kind that the analyte molecules reaching the selected volume element enter into the desired chemical reaction almost completely. This takes place as long as a large surplus of detecting substance is present in the volume element, that is, at the start of the measuring operation corresponding to segment A of the curve in FIG. 2;
(c) determination of a saturation reflectance signal $I^{100\%}$ which corresponds to a complete chemical conversion of the pregiven detecting substance. This effect is measured when the analyte molecules are present in excess compared to the detecting substance, that is, at the end of the measuring operation (corresponding to segment B of the curve of FIG. 2);
(d) the slope is normalized in correspondence to $\Delta I/(I^{100\%} * \Delta t)$; and,
(e) the normalized slope is then proportional to the analyte concentration for constant sample flow.

It is understood that the foregoing description is that of the preferred embodiments of the invention and that various changes and modifications may be made thereto without departing from the spirit and scope of the invention as defined in the appended claims.

What is claimed is:

1. A method for determining the portion of a gaseous or vaporous component in a gas mixture utilizing a detecting substance which can enter into a chemical reaction with said component to produce a coloration of said detecting substance and utilizing a device for evaluating said coloration, the method comprising the steps of:

passing said gas mixture at a constant volume flow through a channel containing said detecting substance;

detecting a reflectance signal I(t) within a defined spatially fixed length segment of said channel;

determining a slope $\Delta I/\Delta t$ at the start of said chemical reaction during a time interval $\Delta t$ in which said detecting substance is present in excess;

determining a saturation reflectance signal $I^{100\%}$ toward the end of said chemical reaction which corresponds to an almost complete chemical conversion of said detecting substance within said length segment; and, determining a normalized slope in correspondence to the formal relationship $$\Delta I/(I^{100\%} * \Delta t)$$

which is proportional to said portion of said gaseous or vaporous component.

2. The method of claim 1, wherein said time interval $\Delta t$ lies between reflectance signal values $I^{30\%}$ and $I^{50\%}$ which correspond to respective reflectance signals of 30% and 50% of said saturation reflectance signal $I^{100\%}$.

3. An arrangement for determining the portion of a gaseous or vaporous component in a gas mixture, the arrangement comprising:

a channel for conducting a constant volume flow of said gas mixture therethrough and containing a detecting substance which can enter a chemical reaction with said component to produce a coloration of said detecting substance;

means for transmitting radiation to a defined spatially fixed length segment of said channel;

means for receiving radiation reflected from said length segment to form a reflectance signal I(t); and, an evaluation unit for receiving said reflectance signal I(t) and being adapted for doing the following: determining a slope $\Delta I/\Delta t$ at the start of said chemical reaction during a time interval $\Delta t$ in which said detecting substance is present in excess; determining a saturation reflectance signal $I^{100\%}$ toward the end of said chemical reaction which corresponds to an almost complete chemical conversion of said detecting substance within said length segment; and, determining a normalized slope in correspondence to the formal relationship $$\Delta I/(I^{100\%} * \Delta t)$$

which is proportional to said portion of said gaseous or vaporous component.

4. The arrangement of claim 3, wherein said channel is a tube made of transparent material having a covering; and, a window formed in said covering having a length corresponding to said fixed length segment.

5. The arrangement of claim 3, wherein said channel is a tube made of transparent material and said fixed length segment being supplemented with optic means for focusing the reflected radiation.

6. The arrangement of claim 5, wherein said optic means is defined by a slit diaphragm.

7. The arrangement of claim 6, wherein said slit diaphragm is mounted forward of said means for receiving radiation.

8. The arrangement of claim 5, wherein said transparent material is glass.

* * * * *

UNITED STATES PATENT AND TRADEMARK OFFICE
CERTIFICATE OF CORRECTION

PATENT NO. : 5,849,591
DATED : December 15, 1998
INVENTOR(S) : Wolfgang Baether, Ingo Kaneblei, Matthias Martens, Andreas Mohrmann and Ingo Pooch It is certified that error appears in the above-identified patent and that said Letters Patent is hereby corrected as shown below:

On the title page, line 2: delete "Bather et al." and substitute -- Bäther et al. -- therefor.

On the title page, under [75]: delete "Bather" and substitute -- Bäther -- therefor.

On the title page, under [73]: delete "United Kingdom" and substitute -- Federal Republic of Germany -- therefor.

On the title page, in the Abstract, line 13: delete "$I^{100}$" and substitute -- $I^{100\%}$ -- therefor.

On the title page, in the Abstract, line 18: delete "$\Delta I/(I^{100}$" and substitute -- $\Delta I/(I^{100\%}$ -- therefor.

Signed and Sealed this

Fourth Day of May, 1999

Attest:

Q. TODD DICKINSON

*Attesting Officer*  *Acting Commissioner of Patents and Trademarks*